United States Patent
Lamraoui (10) Patent No.: US 9,980,807 B2
(45) Date of Patent: May 29, 2018

(54) IMPLANTABLE OCCLUSION SYSTEM COMPRISING A DEVICE FOR DETECTING ATROPHY OF A NATURAL CONDUIT

(71) Applicant: UROMEMS, Grenoble (FR)

(72) Inventor: Hamid Lamraoui, Grenoble (FR)

(73) Assignee: UROMEMS, Grenoble (FR)

( * ) Notice: Subject to any disclaimer, the term of this patent is extended or adjusted under 35 U.S.C. 154(b) by 10 days.

(21) Appl. No.: 14/891,953

(22) PCT Filed: May 21, 2014

(86) PCT No.: PCT/EP2014/060467
§ 371 (c)(1),
(2) Date: Nov. 17, 2015

(87) PCT Pub. No.: WO2014/187870
PCT Pub. Date: Nov. 27, 2014

(65) Prior Publication Data
US 2016/0113754 A1    Apr. 28, 2016

(30) Foreign Application Priority Data

May 21, 2013   (FR) ..................................... 13 54534

(51) Int. Cl.
*A61F 2/04*    (2013.01)
*A61F 2/08*    (2006.01)
(Continued)

(52) U.S. Cl.
CPC .................. *A61F 2/08* (2013.01); *A61B 5/20* (2013.01); *A61B 5/4833* (2013.01);
(Continued)

(58) Field of Classification Search
CPC .............................. A61M 29/02; A61M 29/00
(Continued)

(56) References Cited

U.S. PATENT DOCUMENTS 5,509,888 A    4/1996 Miller
5,704,893 A    1/1998 Timm
(Continued)

FOREIGN PATENT DOCUMENTS

WO    WO-2009027196    3/2009

OTHER PUBLICATIONS

Hajivassiliou, C.A., "A Review of the Complication and results of Implantation of the AMS Artificial Urinary Sphincter", *European Urology*, vol. 35, (1999), 36-44.
(Continued)

*Primary Examiner* — Suzette J Gherbi
(74) *Attorney, Agent, or Firm* — Womble Bond Dickinson (US) LLP (57) ABSTRACT

The invention relates to an occlusive system implantable in an animal or human body to occlude a natural conduit (10) of an animal or human body, comprising:
an occlusive element (9) designed to surround part of the natural conduit (10) to be occluded,
an activation device (2) of said occlusive element (10) for varying the compression exerted by said occlusive element (9) on said conduit (10),
a control unit (7) adapted to urge the activation device (2) so as to exert determined compression on the conduit (10), and
a detection device of atrophy of said natural conduit (10), comprising:
(i) a sensor adapted to measure the compression exerted by the occlusive element (9) on the natural conduit (10), and
(ii) a processing unit adapted to:
determine a representative parameter of strain to be applied to the activation device (2) to achieve determined compression of the conduit (10) by the occlusive element (9),
(Continued)

monitor said parameter over time, and
detect atrophy of the natural conduit (10) when said representative parameter fulfils a predetermined criterion.

29 Claims, 3 Drawing Sheets (51) Int. Cl.
*A61F 2/00* (2006.01)
*A61B 5/00* (2006.01)
*A61B 5/20* (2006.01)
*A61B 17/12* (2006.01)
*A61B 17/135* (2006.01)
*A61B 17/00* (2006.01)
*A61B 90/00* (2016.01)

(52) U.S. Cl.
CPC ...... *A61B 5/6867* (2013.01); *A61B 17/12009* (2013.01); *A61B 17/12013* (2013.01); *A61F 2/0036* (2013.01); *A61F 2/04* (2013.01); *A61B 5/687* (2013.01); *A61B 17/1355* (2013.01); *A61B 2017/00026* (2013.01); *A61B 2017/00199* (2013.01); *A61B 2017/00557* (2013.01); *A61B 2017/00805* (2013.01); *A61B 2090/065* (2016.02); *A61F 2002/047* (2013.01); *A61F 2002/0894* (2013.01); *A61F 2250/0002* (2013.01)

(58) Field of Classification Search
USPC .............................. 623/23.66–23.68; 606/192
See application file for complete search history.

(56) References Cited

U.S. PATENT DOCUMENTS

| | | | |
|---|---|---|---|
| 6,135,945 A | 10/2000 | Sultan | |
| 6,162,238 A | 12/2000 | Kaplan et al. | |
| 8,992,409 B2 * | 3/2015 | Forsell | A61M 1/1068 600/30 |
| 2004/0034275 A1 * | 2/2004 | Forsell | A61L 27/306 600/31 |
| 2007/0156013 A1 | 7/2007 | Birk | |
| 2009/0131959 A1 * | 5/2009 | Rolland | A61F 2/04 606/158 |
| 2009/0240100 A1 * | 9/2009 | Forsell | A61M 1/122 600/30 |
| 2010/0222894 A1 * | 9/2010 | Forsell | A61B 17/1114 623/23.71 |
| 2011/0087337 A1 * | 4/2011 | Forsell | A61B 17/12 623/23.68 |
| 2011/0184230 A1 * | 7/2011 | Forsell | A61F 2/26 600/41 |
| 2011/0208220 A1 | 8/2011 | Snow et al. | |
| 2012/0184980 A1 * | 7/2012 | Anderson | A61F 2/0036 606/192 |

OTHER PUBLICATIONS

Lamraoui, Hamid, et al., "Development of a Novel Artificial Urinary Sphincter: A Versatile Automated Device", *IEEE/ASME Transactions on Mechatronics*, vol. 15, No. 6, (Dec. 2010), 916-924.

Maillet, Frederic, et al., "Management of Artificial Urinary Sphincter Dysfunction", *European Urology*, vol. 46, (2004), 241-246.

Montague, Drogo K., et al., "Artificial Urinary Sphincter Troubleshooting", *Urology*, vol. 58, No. 5, (2001), 779-782.

* cited by examiner

IMPLANTABLE OCCLUSION SYSTEM COMPRISING A DEVICE FOR DETECTING ATROPHY OF A NATURAL CONDUIT

FIELD OF THE INVENTION

The present invention relates to an implantable occlusive system comprising an occlusive element and a device for detecting atrophy of a natural conduit of an animal or human body surrounded by said occlusive element.

This invention applies to any type of occlusion system, including urinary, anal, œsophagal or pyloric artificial sphincters or even gastric rings.

BACKGROUND OF THE INVENTION

The implantation of occlusive systems for fully or partially occluding a natural conduit of a patient is known for different indications. For example, the treatment of urinary incontinence can involve implantation of an artificial sphincter in a patient.

Such a sphincter typically comprises an occlusive element placed around the urethra (in men or women) or sometimes the bladder neck (in women) or the prostate (in men) with the aim of exerting direct or indirect compression on the urethra to prevent urinary leaks, an activation device of said occlusive element to vary compression exerted on the urethra or the bladder neck, as well as a control unit of the activation device.

Such an artificial sphincter is described in particular in [1].

Different technologies of artificial sphincters have been proposed, based especially on different types of occlusive elements and associated activation mode.

According to an embodiment, the occlusive element is an inflatable cuff comprising a variable volume of fluid.

The activation device is a hydraulic device, comprising a reservoir of said fluid and an electromechanical actuator for adding or withdrawing said fluid to compress or decompress the cuff.

Such an artificial sphincter is described for example in [2].

Another example of an artificial sphincter is described in [3].

There is also an electromechanical sphincter, wherein the occlusive element is a band surrounding the urethra or the bladder neck and connected to a cable which exerts more or less strong tension on the band [4].

Due to the compression exerted by the occlusive element, the region located under said element is poorly vascularised, such that the nutrition of the tissues is locally reduced.

This then becomes localised thinning, or atrophy, of compressed tissues.

This atrophy is reversible if it is detected sufficiently early; so, if the compression of the cuff is relaxed for a while, the tissues regenerate and thicken again.

Atrophy of the conduit is the cause of a decrease in efficacy of the occlusive system over time since, as the diameter of the conduit becomes smaller, the occlusive element can no longer achieve the preferred occlusion.

To remedy this, it is proposed either to replace the implanted occlusive element by another one of lesser diameter, or to increase the compression pressure to compensate for the decrease in diameter of the conduit [4], [5], [6].

But, both solutions require a fresh surgical procedure with the attendant risks (infection, etc.) and/or cause also a higher risk of lesion or erosion of the conduit.

A lesion and/or erosion of the tissues—that is, localised rupture of the wall of the conduit—can occur when a considerable degree of atrophy has been attained.

Lesions of non-treated tissues or erosion of tissues can augment the risk of infection, to the extent where bacteria present in the urethra can colonise the affected tissues.

To treat a lesion and/or erosion, it is necessary to perform a fresh surgical procedure to remove the implanted system.

A lesion or erosion of tissues therefore constitutes a serious case of complication of the implantation of the occlusive system.

Erosion is not an isolated phenomenon since meta-analysis on 2606 artificial urinary sphincters [5] showed that 12% of patients implanted with an artificial urinary sphincter suffer from erosion.

It would therefore be desirable to be able to detect atrophy as early as possible to be able to prevent a lesion or erosion of the conduit.

Direct measurement of atrophy, consisting of measuring the diameter of the part of the conduit surrounded by the occlusive element, is not feasible as it would be highly complex to execute in an implanted system.

Currently, none of the occlusive systems proposed on the market can detect any atrophy.

This is therefore only when the patient notices a malfunction of the occlusive system—especially with the appearance of leaks—that the practitioner can consider the conduit has atrophied.

An aim of the present invention is therefore to design an implantable occlusive system for reliably detecting any atrophy and as soon as possible consequently alerting the practitioner or the patient.

BRIEF DESCRIPTION OF THE INVENTION

According to the invention, an occlusive system implantable in an animal or human body for occluding a natural conduit of an animal or human body is proposed, comprising:
  an occlusive element designed to surround part of the natural conduit to be occluded,
  an activation device of said occlusive element for varying the compression exerted by said occlusive element on said conduit,
  a control unit adapted to urge the activation device so as to exert a determined compression on the conduit, and
  a detection device of atrophy of said natural conduit, comprising:
    (i) a sensor adapted to measure compression exerted by the occlusive element on the natural conduit,
    (ii) a processing unit adapted to:
      determine a representative parameter of strain to be applied to the activation device to achieve determined compression of the conduit by the occlusive element,
      monitor said parameter over time, and
      detect atrophy of the natural conduit when said representative parameter fulfils a predetermined criterion.

Particularly advantageously, said predetermined criterion is selected from one of the following conditions or a combination of said conditions:
  the representative parameter is greater than a fixed value,
  the representative parameter is greater than a percentage of a value of said representative parameter measured initially, a value obtained from a mathematical function constructed from a database of values of said representative parameter measured periodically over time is greater than a determined value.

According to an embodiment, said system is an occlusive hydraulic system wherein:
- the occlusive element is an inflatable cuff comprising a variable volume of fluid,
- the activation device comprises a reservoir containing fluid, in fluidic connection with said inflatable cuff,
- the variation of the compression exerted by the cuff on the conduit being made by transfer of an adjustable volume of said fluid between the reservoir and the cuff.

According to an embodiment, the sensor is adapted to measure the compression of the natural conduit directly between the occlusive element and the natural conduit.

According to another embodiment, the sensor is adapted to measure the pressure in a region of the hydraulic circuit and the processing unit is configured to deduce from said measurement the compression exerted by the cuff on the natural conduit.

Particularly advantageously, the monitored representative parameter is the volume of fluid to be transferred from the reservoir to the inflatable cuff to achieve determined compression of the conduit.

The processing unit comprises advantageously a memory wherein is recorded a relation between the pressure in the hydraulic circuit and the volume transferred to the inflatable cuff.

According to an embodiment, the reservoir is a reservoir of variable volume comprising a mobile wall and the processing unit is configured to determine the volume of fluid transferred from measurement of the displacement of said mobile wall.

Advantageously, the system also comprises means for detecting a slow leak in the hydraulic circuit, said means being configured for:
- measurement of the evolution of the pressure in the hydraulic circuit for a determined strain of the activation device,
- detection of a slow leak in the hydraulic circuit when the pressure measured in said circuit for said determined strain of the activation device fulfils a predetermined criterion.

Said predetermined criterion for detecting a slow leak is preferably selected from one of the following conditions or a combination of said conditions:
- the pressure in the hydraulic circuit is less than a fixed value,
- the pressure in the hydraulic circuit is less than a percentage of a value of the pressure measured initially for said determined strain of the activation device, and
- a value coming from a mathematical function constructed from a database of values of said pressure for said strain of the activation device, said pressure being recorded periodically over time, is less than a determined value.

According to another embodiment, the occlusive system is a mechanical occlusive system wherein:
- the occlusive element is a band of variable length surrounding the natural conduit,
- the activation device comprises a mechanical transmission element connecting said band and an actuator adapted to adjust the travel of said mechanical transmission element,
- the variation of the compression exerted by the band on the conduit being made by the adjustment of the travel of said mechanical transmission element.

In this case, the sensor is advantageously adapted to measure the mechanical tension of said mechanical transmission element and the processing unit is configured to deduce from said measured mechanical tension the compression exerted by the band on the natural conduit.

Preferably, said representative parameter is the travel of said mechanical transmission element between the actuator and the occlusive band for attaining a determined compression of the conduit.

The processing unit advantageously comprises a memory wherein a relation between the travel of the mechanical transmission element and the mechanical tension of said transmission element or the compression exerted by the band is recorded.

Preferably, the representative parameter is defined for a determined condition of the patient, the occlusive system comprising a sensor adapted to detect said determined condition of the patient.

According to an embodiment, the processing unit is included in the control unit of the occlusive system.

Advantageously, the occlusive system further comprises means for sending an alarm to a user if the detection criterion of atrophy of the natural conduit is fulfilled.

According to a particular application of the invention, said occlusive system consists of an artificial urinary sphincter.

The invention executes a method for detection of the atrophy of a natural conduit surrounded by such an occlusive system, said method comprising:
- measurement—direct or indirect—of the compression exerted by the occlusive element on the natural conduit,
- determination of a representative parameter of strain to be applied to the activation device to obtain determined compression of the conduit by the occlusive element, and monitoring of said parameter over time,
- detection of atrophy of the natural conduit when said representative parameter fulfils a predetermined criterion.

For example, said predetermined criterion is selected from one of the following conditions or a combination of said conditions:
- the representative parameter is greater than a fixed value,
- the representative parameter is greater than a percentage of a value of said representative parameter measured initially,
- a value obtained from a mathematical function constructed from a database of values of said representative parameter measured periodically over time is greater than a determined value.

According to an embodiment, the compression of the natural conduit is measured directly between the occlusive element and the natural conduit.

According to an embodiment of the invention, the occlusive system comprises a hydraulic circuit wherein:
- the occlusive element is an inflatable cuff comprising a variable volume of fluid,
- the activation device comprises a reservoir containing fluid, in fluidic connection with said inflatable cuff,
- variation in compression exerted by the cuff on the conduit being done by transfer of an adjustable volume of said fluid between the reservoir and the cuff.

According to an embodiment, the pressure is measured in a region of said hydraulic circuit and the compression exerted by the cuff on the natural conduit.

The representative parameter can be the volume of fluid to be transferred from the reservoir to the inflatable cuff to attain determined compression of the conduit.

Preferably, a mathematical relation between the pressure in the hydraulic circuit and the volume transferred to the inflatable cuff is set up in advance.

According to an embodiment, the reservoir is a reservoir of variable volume comprising a mobile wall and the volume of fluid transferred is determined from measurement of the displacement of said mobile wall.

Particularly advantageously, a method for detecting a slow leak in the hydraulic circuit is also conducted, which comprises:
- measurement of the evolution of the pressure in the hydraulic circuit for determined strain of the activation device,
- the detection of a slow leak in the hydraulic circuit when the pressure measured in said circuit for said determined strain of the activation device fulfils a predetermined criterion.

For detecting such a slow leak, said predetermined detection criterion can be selected from one of the following conditions or a combination of said conditions:
- the pressure in the hydraulic circuit is less than a fixed value,
- the pressure in the hydraulic circuit is less than a percentage of a value of the pressure measured initially for said determined strain of the activation device, and
- a value obtained from a mathematical function constructed from a database of values of said pressure for said strain of the activation device, said pressure being recorded periodically over time, is less than a determined value.

According to another embodiment of the invention, the occlusive system comprises a mechanical system wherein:
- the occlusive element is a band of variable length surrounding the natural conduit,
- the activation device comprises a mechanical transmission element connecting said band and an actuator adapted to adjust the travel of said mechanical transmission element,
- the variation in compression exerted by the band on the conduit being done by adjustment of the travel of said mechanical transmission element.

According to an embodiment, the tension of said mechanical transmission element is measured and one deduced from this the compression exerted by the band on the natural conduit.

The representative parameter can be the travel of said mechanical transmission element between the actuator and the occlusive band to achieve determined compression of the conduit.

Preferably, a relation between the travel of the mechanical transmission element and the tension of said transmission element or the compression exerted by the band is set up in advance.

According to a particular embodiment of the invention, said representative parameter is defined for a determined condition of the patient and the method comprises the detection of said determined condition of the patient.

Advantageously, said method is conducted by the control unit of the occlusive system.

The method can further comprise sending an alarm to a user if the detection criterion of atrophy of the natural conduit is fulfilled.

BRIEF DESCRIPTION OF THE DRAWINGS

Other characteristics and advantages of the invention will emerge from the following detailed description, in reference to the attached drawings, wherein.

DETAILED DESCRIPTION OF THE INVENTION

In general, the occlusive system comprises an occlusive element surrounding a natural conduit to be occluded.

Depending on the application of the relevant occlusive system, the conduit to be occluded can be a urinary conduit (especially urethra or bladder neck), or anal, œsophagal, pyloric conduit or even stomach (case of a gastric ring).

The occlusion of said conduit can be total (case of a urinary sphincter designed to prevent urinary leaks) or partial (case of a gastric ring designed to limit food entering the stomach).

The artificial sphincter also comprises an activation device for adjusting compression exerted by the occlusive element.

There is therefore a link between the occlusive element and the activation device, which depends on the mode of action of said occlusive element.

For example, in the case of an occlusive hydraulic system the occlusive element is an inflatable cuff likely to contain an adjustable volume of fluid and the activation device comprises a fluid reservoir, the link between the cuff and the activation device comprising tubing for transferring fluid bidirectionally from the cuff to the reservoir depending on whether the aim is to increase or decrease the compression exerted.

In the case of an electromechanical occlusive system, the occlusive element is in the form of a band whereof the tension is adjustable and the activation device comprises an actuator adapted to adjust tension of the occlusive band, the link between the band and the activation device being ensured by a cable or any other means for applying variable tension to the occlusive band.

In the oldest occlusive systems this activation device is controlled manually by the patient, for example by pressure exerted on a pump device arranged under the skin.

Currently, more refined systems are being developed to prevent the patient from exerting manual pressure on the pump for controlling the occlusive element.

The occlusive system comprises a control unit, also implantable in the body of the patient, adapted to control the activation device of the cuff.

There are currently different types of occlusive systems utilising different technologies of occlusive elements (hydraulic, mechanical, etc.) and different associated activation technologies (piezoelectric actuator, cables, memory shape devices, etc.).

These different occlusive systems are known to those skilled in the art.

As for artificial urinary sphincters, reference could be made for example to the following documents [1] to [4] cited above or even to documents [8] and [9].

The invention is not limited to any one particular technology of occlusive system.

The activation device and the control unit are advantageously included in a case implantable in the body of the patient designed to protect it.

The case is typically made of biocompatible material.

Figure 1:
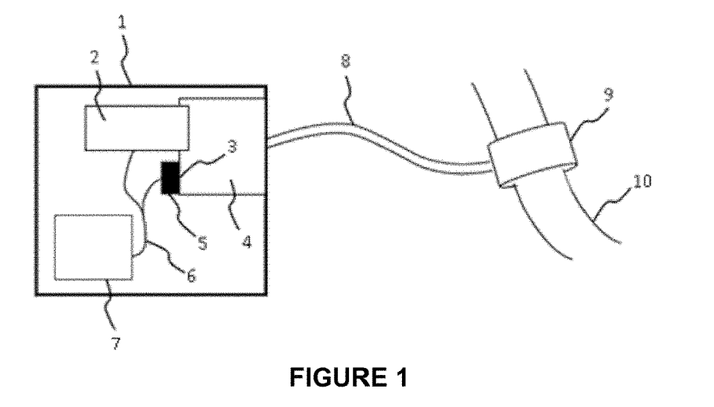
FIG. 1 is a block diagram of an occlusive hydraulic system associated with a detection device of atrophy according to an embodiment of the invention.

FIG. 1 is a block diagram of an occlusive hydraulic system 1 associated with a detection device of atrophy according to an embodiment of the invention.

The occlusive element 9 is in the form of an inflatable cuff likely to be filled with a variable quantity of fluid, with variation in fluid pressure inside the cuff varying compression exerted on the natural conduit 10 to be occluded.

A fluid reservoir 4, for example of saline solution, is arranged in fluidic connection with the cuff, by means of tubing 8.

The assembly of the cuff 9, the reservoir 4 and the tubing 2 forms the hydraulic circuit of the occlusive system 1.

This hydraulic circuit allows transferring some of the fluid from the reservoir to the cuff to increase compression exerted on the conduit 10 and inversely to transfer some of the fluid from the cuff to the reservoir to decrease compression exerted by the cuff on the conduit 10.

For this purpose, the occlusive system also comprises an activation device 2 for performing this transfer of fluid and thus vary compression exerted by the cuff on the conduit 10.

Particularly advantageously, the reservoir 4 has a variable volume.

For example, but non-limiting, the variation in volume can be achieved by moving a wall of the reservoir, the activation device 2 comprising an actuator for moving said wall.

Therefore, the reservoir can comprise a rolling membrane, a piston, bellows or any other means for varying its volume.

Those skilled in the art can select from existing actuators an adequate actuator as a function of the planned implementation with respect to the reservoir.

A non-limiting example is a piezoelectric actuator, etc.

Even though it is not illustrated here, the activation device comprises a sensor for measuring the action exerted on the reservoir.

For example, if actuation consists of displacement of a mobile wall of the reservoir, said sensor can consist of a position sensor for determining the position of the mobile wall.

Calibrating determines both the relation between the position of the mobile wall and the variation in volume of the reservoir as well as the relation between the variation in volume of the reservoir and the pressure in the hydraulic circuit and finally between the pressure in the hydraulic circuit and the compression exerted on the conduit to be occluded.

The relation between the pressure in the hydraulic circuit and the volume transferred from the reservoir to the inflatable cuff can optionally be expressed in the form of a mathematical relation.

Depending on the case, this relation can be linear or not.

Therefore, it is possible to determine the displacement to be imposed on the mobile wall to obtain a given pressure of fluid in the hydraulic circuit in light of obtaining a given compression of the conduit 10.

In this case, displacement control of the activation device is based on measurement of the pressure in the hydraulic circuit.

For this reason, in the embodiment illustrated in FIG. 1 a pressure sensor 5 is arranged on a wall of the reservoir 4 so as to provide measurement of the fluid pressure in the reservoir.

The occlusive system 1 also comprises a control unit 7 adapted to urge the activation device 2 so as to exert determined compression on the conduit 10.

The link 6 between the control unit 7 and the activation device 2 has been illustrated in wired form in FIG. 1, but it is understood that it could be operated wireless, according to the technology selected by those skilled in the art.

There is also a link 6 (wired or not) between the sensor 5 and the control unit 7.

Figure 2:
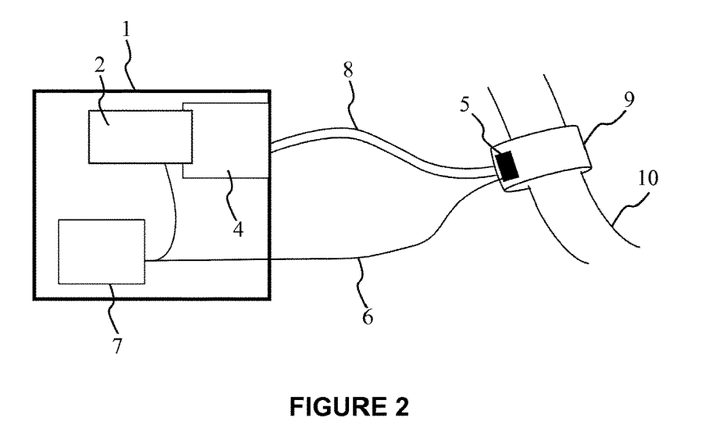
FIG. 2 is a block diagram of an occlusive hydraulic system associated with a detection device of atrophy according to another embodiment of the invention.

FIG. 2 illustrates another embodiment of an occlusive hydraulic system 1.

The components designated by the same reference signs as in FIG. 1 fulfil the same function and therefore will not be described in greater detail.

Relative to the device illustrated in FIG. 1, the sensor 5 for measuring the pressure in the hydraulic circuit is not arranged on a wall of the reservoir 4 but on the occlusive cuff 9, so as to directly measure the pressure on the conduit 10.

It is understood that a pressure sensor could be used in any other place of the compression system without as such departing from the scope of the present invention.

Figure 3:
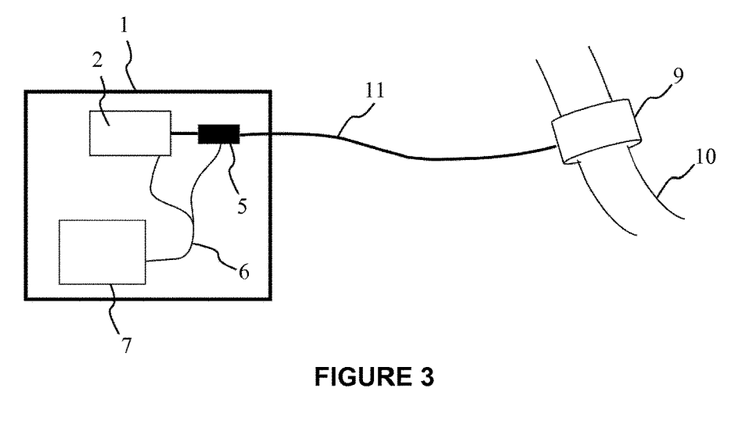
FIG. 3 is a block diagram of an occlusive system mechanical associated with a detection device of atrophy according to another embodiment of the invention.

FIG. 3 is a block diagram of an electromechanical occlusive system 1 associated with a detection device of atrophy according to an embodiment of the invention.

The occlusive element 9 is in the form of a band placed around the conduit 10 to be occluded, a variation in tension of the band varying the compression exerted on the natural conduit 10 to be occluded.

The band is connected by a mechanical transmission element 11 to an activation device 2.

For example, the element 11 is a cable.

The activation device is adapted to vary the travel and/or tension of the mechanical transmission element 11 with a view to increasing or decreasing compression exerted on the conduit 10 by the occlusive band 9.

Those skilled in the art can select from existing actuators an adequate actuator as a function of the selected mechanical transmission element.

A non-limiting example is a piezoelectric actuator, etc.

Calibrating determines both the relation between the travel and the tension of the mechanical transmission element as well as the relation between the tension of the occlusive band and the compression exerted on the conduit to be occluded.

The relation between the travel and the tension of the mechanical transmission element can optionally be expressed in the form of a mathematical relation.

Depending on the case, this relation can be linear or not.

Therefore, it is possible to determine the travel to be imposed on the mechanical transmission element to obtain a given tension of the occlusive band in light of obtaining a given compression of the conduit 10.

In this case, displacement control of the activation device is based on measurement of the tension of the mechanical transmission element.

For this reason, as illustrated in FIG. 3, a tension sensor 5 is arranged on the mechanical transmission element so as to provide measurement of the tension of said element.

The occlusive system further comprises a control unit 7 adapted to urge the activation device 2 so as to exert a determined compression on the conduit 10.

The link 6 between the control unit 7 and the activation device 2 has been illustrated in wired form in FIG. 3, but it is understood that it could be used wireless, according to the technology selected by those skilled in the art.

There is also a link 6 (wire or not) between the sensor 5 and the control unit 7.

In another embodiment, the occlusive system is based on a peristaltic pump for transferring fluid contained in a reservoir from or to the occlusive cuff.

The embodiments described hereinabove are not designed to limit the invention and other activation means and other sensors could be selected without departing from the scope of the present invention.

Measuring the Compression Exerted on the Conduit to be Occluded

Measurement of compression exerted on the conduit to be occluded can be done directly on said conduit or, preferably and generally more easily to implement, indirectly, by a value measured at the level of the occlusive element, of the activation device or of the link between the occlusive element and the activation device.

Therefore, as already indicated above, the pressure in the hydraulic circuit (measured at the level of a wall of the reservoir or at the level of the cuff) or the tension of the occlusive band in the case of an electromechanical system, provides an indication of compression of the conduit.

The relation between the level of compression of the conduit and the pressure in the hydraulic circuit or the tension of the occlusive band is set in advance, as a function of the mode of activation and materials used during designing of the device.

Calibrating of this relation can also be done in some cases by taking pressure measurements in the conduit to be occluded at different pressures in the hydraulic circuit, or at different tensions, depending on the embodiment selected.

Representative Parameter

In addition, a representative parameter of strain to be applied to the activation device to obtain a determined compression of the conduit to be occluded is determined.

Therefore, in the case of an occlusive hydraulic system such as described hereinabove, the representative parameter can be defined as being the position of the mobile wall of the reservoir relative to a reference position to obtain a determined compression of the conduit.

For example, the reference position can be the position of the wall wherein no compression is exerted on the conduit.

This reference position can be considered as an initial stop position corresponding to an empty occlusive cuff.

The representative parameter can be defined as the position of the mobile wall wherein a given compression of the conduit is attained.

The representative parameter can also be defined as being the distance to cover by the mobile wall of the reservoir to move from the initial stop position to the position for attaining said given compression of the conduit to be occluded.

Alternatively, the representative parameter can be defined as being the volume of fluid in the reservoir to obtain maximal compression of the conduit, the reference volume being the maximal volume of the reservoir.

In the case of an electromechanical occlusive system, the representative parameter can be defined as the travel to be imposed on the mechanical transmission element to obtain tension corresponding to a given compression of the conduit to be occluded.

In the case of an occlusive system based on a peristaltic pump, the representative parameter can be defined as the angular travel described by the pump relative to a reference position to obtain a given compression of the conduit.

It can be seen that, irrespective of the type of occlusive system, the value of the representative parameter can vary depending on the condition of the patient, for example depending on his posture.

The representative parameter could therefore be defined for a determined condition of the patient and be monitored over time and be registered only when the patient is in an adequate condition.

Monitoring of the Representative Parameter Over Time

In case of atrophy of the conduit to be occluded, a drift of the representative parameter of the patient occurs.

This drift is due to the fact that, given the atrophy, the thickness of the wall of the conduit decreases.

Consequently, to exert the same given compression of the conduit it is necessary to apply greater strain on the activation device.

For example, it is necessary to put more fluid in the cuff (in the case of a hydraulic system) or apply greater displacement to the cable linked to the occlusive band (in the case of an electromechanical system).

The monitoring of the representative parameter over time therefore detects, by way of a drift of the value of this parameter, atrophy of the conduit to be occluded.

The representative parameter is therefore monitored over time and recorded in a memory of the processing unit.

Particularly advantageously, said parameter is measured when the patient is in a predetermined condition, or during transition from a first predetermined condition to a second predetermined condition of the patient.

<<Predetermined condition>> means a particular posture (for example standing upright, lying or seated) and/or performing a particular action (for example urination in the case of an artificial urinary sphincter).

For example, when the patient is lying and immobile, the system can reduce the compression exerted on the conduit to be occluded.

Such is the case for example in an artificial urinary sphincter using a model predictive of urinary leaks such as described in [1], wherein the compression exerted on the conduit is adjusted as a function of the activity of the patient: application of weak compression of the urethra is in fact enough when the patient is asleep.

In this particular case, the representative parameter of strain to be applied can be the volume to be injected into the cuff (in the case of a hydraulic system) or the travel to be applied to the cable (in the case of an electromechanical system) to move from a given compression corresponding to the situation <<patient lying>> to a given compression which is greater and corresponding to the <<patient upright>> situation, the values of said compressions being configured by the user.

In another case, measurement of the representative parameter can be done during urination.

The patient can be fitted with one or more sensors for detecting the predetermined condition or the predetermined conditions mentioned hereinabove.

By way of non-limiting example, to determine the posture of the patient, an accelerometer, a gyroscope and/or an inclinometer could be used.

The man skilled in the art is able to define the sensor(s) adapted to detect a predetermined condition or predetermined conditions of the patient.

Detection of Atrophy Criterion

The detection criterion of atrophy can be selected from different possibilities, some of which will be described hereinbelow.

According to a first embodiment of the invention, the detection criterion of atrophy is fulfilled when the representative parameter is greater than a fixed value, independent of the patient, fixed arbitrarily.

According to another embodiment, the detection criterion of atrophy is fulfilled when the representative parameter is greater than a percentage of a value of the parameter measured initially.

For example, the value of the representative parameter is measured after implantation of the occlusive system in the patient, and this value is selected as reference.

A percentage of this reference value is also selected as being the value beyond which atrophy is detected.

For example, this percentage could be of the order of 130 to 180%.

An advantage of this criterion is that it considers the individual situation of the patient, since it is based on measurement made on the patient on initialisation of the detection process.

According to another embodiment of the invention, the detection criterion of atrophy involves comparison, not of the representative parameter itself, but a function of said parameter, with a determined value.

Therefore, the value to be compared to said determined value can be a value obtained from a mathematical function constructed from a database of values of said representative parameter measured periodically over time.

Since atrophy evolves slowly initially then more rapidly, a criterion on the evolution of the atrophy of tissues over time can be advantageous.

By way of non-limiting example, by fixing a criterion based on the derivative of the evolution curve of the representative parameter, it is possible to warn the clinician of atrophy when the latter evolves rapidly, that is, when this derivative reaches or exceeds a determined value.

It is also feasible to define a more complex decision criterion which simultaneously takes into account different conditions by combining different criteria including those especially presented in the preceding paragraphs.

Figure 4:
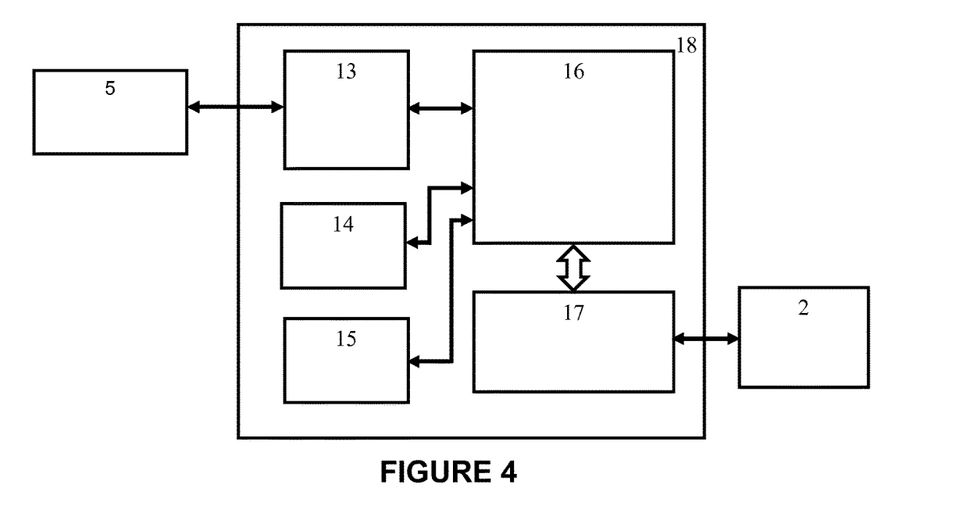
FIG. 4 is a block diagram of the architecture of the control unit of an occlusive system incorporating a detection device of atrophy.

FIG. 4 illustrates an embodiment of the general architecture of the processing unit for detection of a possible atrophy.

The processing unit 18 comprises a microprocessor 16 adapted to implement an algorithm for determining, from measurements of the sensor(s), the value of the representative parameter.

For this reason, the microprocessor 16 communicates with at least one sensor 5 by means of an interface 13.

Communication is shown by arrows and can be done by a wired link or by a wireless link, according to known protocols.

The processing unit 18 also comprises a memory 14 wherein are recorded the detection program, the values of the representative parameter, and the conditions to be fulfilled so that atrophy is detected.

The processing unit further comprises one or more clocks 15.

The microprocessor 16 is connected to the interface 13, the memory 14 and the clock 15.

The microprocessor 16 further communicates with the activation device 2 by means of an interface 17.

Figure 5A:
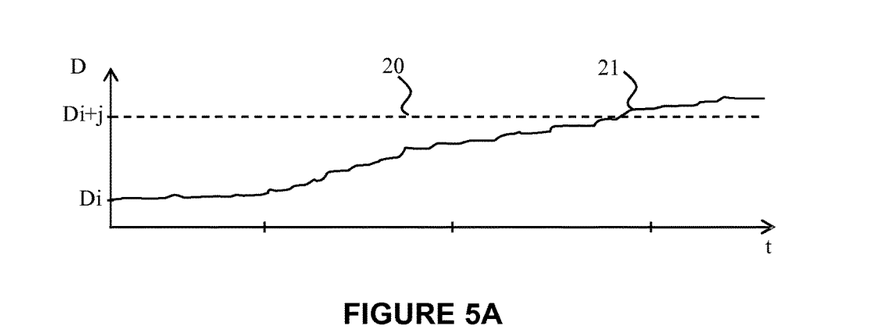
FIG. 5A illustrates an example of curve of a variation of the representative parameter of the strain to be applied to the activation device to obtain determined compression of the conduit by the occlusive element as a function of time.
Figure 5B:
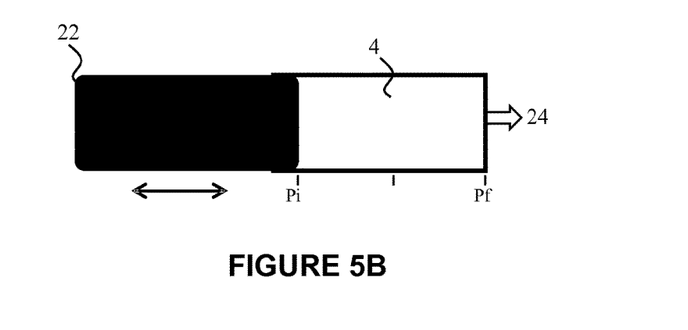
FIG. 5B presents the different positions of the piston in the case of an occlusive hydraulic system.

FIGS. 5A and 5B illustrate an example of detection of atrophy in the case of an occlusive hydraulic system.

In the embodiment illustrated in FIG. 5B, the reservoir 4 has a variable volume due to displacement of a piston 22.

The travel of the piston is defined by two positions limits: the position Pi, corresponding to an initial stop of the piston wherein the occlusive cuff is empty, and the position Pf, corresponding to a final stop of the piston wherein the occlusive cuff is filled with fluid so as to exert maximal compression of the piston.

Arrow 24 indicates the output direction of the fluid from the reservoir to the occlusive cuff.

The position of the piston for exerting a given compression on the conduit is between the positions Pi and Pf.

In this case, it is the distance between said position and a reference position corresponding to the position Pi which is defined as the representative parameter of the strain to be applied to the activation device to obtain a given compression of the conduit.

The initial distance is designated by Di.

The graph of FIG. 5A presents the evolution 21 of the distance D over time, in the event where atrophy occurs.

As can be seen on this graph, the distance D grows progressively from the initial value Di.

When the curve of the distance D reaches a predetermined threshold 20 corresponding to a value of distance Di+j, it is considered that atrophy is detected.

If needed, an alert is sent by the processing unit to the attention of the patient and/or of the practitioner.

Detection of a Slow Leak in the Hydraulic Circuit

In the case of an occlusive hydraulic system, a slow leak occurring in the hydraulic circuit is likely to modify over time the strain to be applied to the activation device to obtain a determined compression of the conduit to be occluded.

<<Slow leak>> in the present text means a loss of liquid in a small quantity and stretching over a long period (at least several days, but more generally of the order of several months), causing progressive decrease of the pressure in the hydraulic circuit.

By opposition, a leak is considered as rapid if it causes a sharp decrease of pressure in the hydraulic circuit.

Therefore, a rapid leak is detectable as soon as the triggering event has taken place (for example, disconnection of the tubing connecting the cuff to the fluid reservoir) or shortly after (for example, substantial damage of one of the materials ensuring sealing).

On the contrary, a slow leak becomes detectable only several days, or even several months after the occurrence of the breakdown which is the cause.

Such slow leaks can have different causes, including:
damage of a mechanical element of the hydraulic circuit, for example cracking of an element,
a defect of the connection of the tubing to the reservoir or to the occlusive cuff,
the porosity of the material constituting the tubing and/or the occlusive cuff (generally made of silicone) and inadequate concentration of the saline solution contained in the hydraulic circuit, generating a concentration gradient between the extracellular medium and the hydraulic circuit, which causes diffusion of water from the least concentrated medium to the most concentrated medium. In particular, if the fluid contained in the hydraulic circuit is insufficiently concentrated (hypotonic) relative to the external medium, the water will tend to diffuse to the exterior of the hydraulic circuit, leading to a decrease in the volume in said circuit.

Therefore, if the representative parameter is a distance to be covered by the mobile wall of the reservoir for exerting a given compression on the conduit, the effect of a slow leak will be that this distance augments over time.

The effect of this drift is to detect a variation of the representative parameter defined above, without atrophy effectively occurring, which causes false detection.

To remedy this possible problem (which relates only to occlusive hydraulic systems), the invention proposes, in a particular embodiment detecting a possible slow leak, which distinguishes a slow leak from possible atrophy.

To that end, the method described hereinbelow is implemented.

In general, detection of a slow leak involves monitoring of the pressure in the hydraulic circuit over time and comparison of said pressure or a function of said pressure with a predetermined criterion.

Measuring of the Pressure in the Hydraulic Circuit

Measuring of the pressure in the hydraulic circuit can be done at any point of said circuit, for example with one or more of the pressure sensors mentioned above.

In the present invention, the focus is on evolution of the pressure in the hydraulic circuit in a particular situation, corresponding to a determined strain of the activation device.

This determined strain depends on the type of activation device used in the occlusive system.

For example, when the reservoir comprises a mobile wall for varying its volume and the activation device is adapted to move said wall by a determined distance, the determined strain for which the pressure in the hydraulic circuit is monitored can correspond to an open stop position of said wall (corresponding to a maximal volume of the reservoir, the occlusive cuff being empty).

When a slow leak occurs in the hydraulic circuit, the pressure in the hydraulic circuit for this determined position of the wall tends to drop, and can even become negative.

Similarly, in the event where the activation device comprises a peristaltic pump, the strain for which the evolution of the pressure in the hydraulic circuit is monitored can be defined for a reference position of said pump for obtaining a given compression of the conduit.

Monitoring of the Pressure Over Time

To detect a possible slow leak in the hydraulic circuit, the pressure in the hydraulic circuit for the strain predetermined described hereinabove is recorded periodically.

The periodicity of measurement is not necessarily regular, that is, time intervals of different lengths can span between two consecutive measurements.

Also, recording of the pressure is not necessarily done each time the strain predetermined is encountered, but can optionally be done less often, according to a predetermined frequency/

Also, the periodicity of measurement can depend on the type of occlusive system in question.

For example, for a urinary or anal occlusive system, at least once per day there is opening of the occlusive cuff to allow for urination or defecation.

Consequently, for these systems the pressure in the hydraulic circuit can be monitored daily by recording the pressure in the hydraulic circuit during at least one urination or defecation.

In other systems (for example gastric rings), the system can be calibrated either during control performed by the user or autonomously by placing the activation device in a reference position, in conditions which do not affect the function of the occlusive system.

Criterion for Detecting a Slow Leak

The detection criterion of a slow leak can be selected from different possibilities, some of which will be described hereinbelow.

According to a first embodiment of the invention, the detection criterion of such a slow leak is fulfilled when the pressure in the hydraulic circuit becomes less than a fixed value, independent of the patient, fixed arbitrarily.

This threshold value is preferably zero or negative.

According to another embodiment, the detection criterion of a slow leak is fulfilled when the pressure in the hydraulic circuit becomes less than a percentage of the value of the pressure measured initially.

For example, the value of the pressure in the hydraulic circuit is measured for a determined strain of the activation device after implantation of the occlusive system in the patient, and this value is selected as reference.

A percentage of this reference value is selected as being the value beyond which a slow leak is detected.

For example, this percentage could be of the order of 20%.

This value can be also negative and proportional to one or more parameters of the system.

An advantage of this criterion is that it considers the individual situation of the patient, since it is based on a measurement taken on the patient on initialisation of the detection process.

According to another embodiment of the invention, the detection criterion of a slow leak involves comparison, not of the pressure measured itself, but a function of said pressure, with a determined value.

Therefore, this value to be compared to said determined value can be a value obtained from a mathematical function constructed from a database of values of pressure measured periodically over time.

Therefore, the presence of a slow leak can be considered for example when the product x.P drops below a threshold value, x being a parameter able to evolve over time to take into account the ageing of materials of the occlusive system, and P the pressure measured in the hydraulic circuit for a given strain.

For example, this threshold value can be negative in particular.

It is also feasible to define a more complex detection criterion, which simultaneously takes into account different conditions by combining different criteria including those especially presented in the foregoing paragraphs.

In general, a negative threshold value has the advantage of distinguishing with certainty atrophy of a slow leak.

In fact, in the presence of atrophy, even if a variation occurs of the strain to be applied to the activation device to obtain a determined compression of the conduit, the overall volume of fluid in the hydraulic circuit remains substantially the same and the pressure in the hydraulic circuit will always remain positive for a determined strain of the activation device.

Observation of pressure less than a zero or negative threshold value in the hydraulic circuit for a determined strain of the activation device is therefore characteristic of a slow leak.

This method can be used in the processing unit illustrated in FIG. 4.

Figure 6:
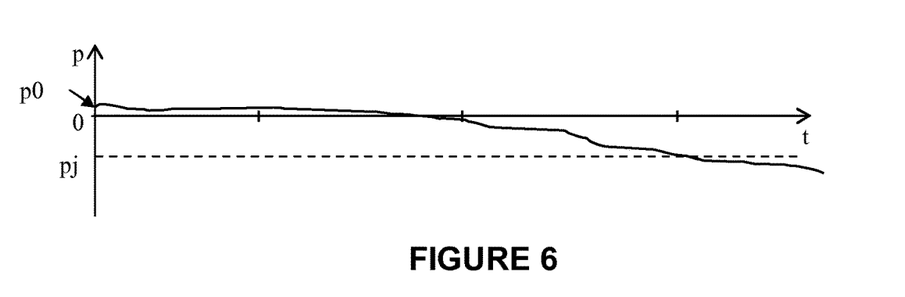
FIG. 6 illustrates an example of curve of a variation of the pressure in the hydraulic circuit as a function of time in the case of a slow leak.

FIG. 6 illustrates an example for detecting a slow leak in an occlusive hydraulic system.

As in the embodiment illustrated in FIG. 5B, the reservoir 4 has a variable volume due to the displacement of a piston 22.

The travel of the piston is defined by two positions limits: the position Pi, corresponding to an initial stop of the piston wherein the occlusive cuff is empty, and the position Pf, corresponding to a final stop of the piston wherein the occlusive cuff is filled with fluid so as to exert maximal compression of the conduit.

Focus is on the variation in pressure in the hydraulic circuit when the piston is in the position Pi.

The pressure in the hydraulic circuit on initialisation of the occlusive system is noted p0.

The graph of FIG. 6 presents the evolution of pressure p over time when the piston is in the position Pi, in the event where a slow leak happens.

As can be seen on this graph, the pressure p drops progressively from the initial value p0.

When the curve of the pressure p reaches a predetermined threshold noted pj, it is considered that a slow leak is detected.

It is possible to differentiate a slow leak of the system of atrophy from the natural conduit.

When appropriate, an alert is sent by the processing unit to the attention of the patient and/or of the practitioner.

The practitioner can then decide to add a fresh volume of fluid to the hydraulic circuit, which avoids a fresh surgical procedure.

This addition can be made via an injection port which is generally provided on the hydraulic circuit, in particular on the reservoir.

The injection port can comprise a septum arranged in one of the walls of the reservoir which is placed opposite the skin of the patient, such that the practitioner can introduce a needle into the reservoir through the skin.

The septum is made of biocompatible material ensuring sealing of the reservoir while and after the needle is removed.

Silicone is generally used for this usage.

REFERENCES

[1] WO 2009/027196
[2] Development of a Novel Artificial Urinary Sphincter, H. Lamraoui and al, IEEE/ASME Transactions on Mechatronics, Vol. 15, No. 6, December 2010
[3] U.S. Pat. No. 6,162,238
[4] U.S. Pat. No. 5,704,893
[5] F. Maillet, J.-M. Buzelin, O. Bouchot, and G. Karam, "Management of artificial urinary sphincter dysfunction," European Urology, vol. 46, no. 2, pp. 241-246, August 2004.
[6] C. Hajivassiliou, "A review of the complications and results of implantation of the AMS artificial urinary sphincter," European Urology, vol. 35, no. 1, pp. 36-44, 1999.
[7] D. K. Montague and K. W. Angermeier, "Artificial urinary sphincter troubleshooting," Urology, vol. 58, no. 5, pp. 779-782, November 2001.
[8] U.S. Pat. No. 5,509,888
[9] U.S. Pat. No. 6,135,945

The invention claimed is:

1. An occlusive system implantable in an animal or human body for occluding a natural conduit of an animal or human body, comprising:
an occlusive element designed to surround part of the natural conduit to be occluded, wherein the occlusive element is one of an inflatable cuff and a band of variable length,
an activation device of said occlusive element for varying the compression exerted by said occlusive element on said conduit,
a control unit configured to urge the activation device so as to exert determined compression on the conduit, and
a detection device of atrophy of said natural conduit, comprising:
a compression sensor configured to measure the compression exerted by the occlusive element on the natural conduit,
a displacement sensor configured to measure a displacement parameter applied to the activation device;
a memory configured to record measurement data from said displacement sensor; and
a processing unit configured to:
apply a controlled displacement parameter to the activation device to obtain a determined compression of the conduit by the occlusive element,
record in the memory measurement data of said controlled displacement parameter over time by the displacement sensor, and
based on the data recorded in the memory, detect atrophy of the natural conduit when said controlled displacement parameter fulfils a predetermined criterion recorded in the memory.

2. The system of claim 1, wherein said predetermined criterion is selected from one of the following conditions or a combination of said conditions:
the displacement parameter is greater than a fixed value,
the displacement parameter is greater than a percentage of a value of said displacement parameter measured initially,
a value obtained from a mathematical function constructed from a database of values of said displacement parameter measured periodically over time is greater than a determined value.

3. The system of claim 1, said system being an occlusive hydraulic system wherein:
the occlusive element is an inflatable cuff comprising a variable volume of fluid,
the activation device comprises a reservoir containing fluid, in fluidic connection with said inflatable cuff,
the variation in compression exerted by the cuff on the conduit is done by transfer of an adjustable volume of said fluid between the reservoir and the cuff.

4. The system of claim 3, wherein the compression sensor is configured to measure the compression of the natural conduit directly between the occlusive element and the natural conduit.

5. The system of claim 3, wherein the compression sensor is configured to measure the pressure in a region of said hydraulic circuit and the processing unit is configured to deduce from said measurement the compression exerted by the cuff on the natural conduit.

6. The system of claim 3, wherein said displacement parameter is defined based on a volume of fluid to be transferred from the reservoir to the inflatable cuff to achieve determined compression of the conduit.

7. The system of claim 3, wherein the processing unit comprises a memory wherein a relation between the pressure in the hydraulic circuit and the volume transferred to the inflatable cuff is recorded.

8. The system of claim 3, wherein the reservoir is a reservoir of variable volume comprising a mobile wall, the displacement sensor is configured to measure a position of said mobile wall and wherein the processing unit is configured to determine the volume of fluid transferred from measurement of the displacement of said mobile wall.

9. The system of claim 3, further comprising means for detecting a slow leak in the hydraulic circuit, said means being configured for:
measuring the evolution of the pressure in the hydraulic circuit for a determined displacement of the activation device,
detecting a slow leak in the hydraulic circuit when the pressure measured in said circuit for said determined displacement of the activation device fulfils a predetermined criterion.

10. The system of claim 9, wherein said predetermined criterion for detecting a slow leak is selected from one of the following conditions or a combination of said conditions:
the pressure in the hydraulic circuit is less than a fixed value,
the pressure in the hydraulic circuit is less than a percentage of a value of the pressure measured initially for said determined displacement of the activation device, and
a value obtained from a mathematical function constructed from a database of values of said pressure for said displacement of the activation device, said pressure being recorded periodically over time, is less than a determined value.

11. The system of claim 1, said system being a mechanical occlusive system wherein:
the occlusive element is a band of variable length surrounding the natural conduit
the activation device comprises a mechanical transmission element connecting said band and an actuator configured to adjust the travel of said mechanical transmission element,
the variation of the compression exerted by the band on the conduit is done by adjustment of the travel of said mechanical transmission element.

12. The system of claim 11, wherein the compression sensor is configured to measure the mechanical tension of said mechanical transmission element and wherein the processing unit is configured to deduce from said measured mechanical tension the compression exerted by the band on the natural conduit.

13. The system of claim 11, wherein said displacement parameter is the travel of said mechanical transmission element between the actuator and the occlusive band to reach determined compression of the conduit.

14. The system of claim 11, wherein the processing unit comprises a memory wherein a relation between the travel of the mechanical transmission element and the mechanical tension of said transmission element or the compression exerted by the band is recorded.

15. The system of claim 1, wherein said displacement parameter is defined for a determined condition of the patient and said occlusive system comprises a patient condition sensor configured to detect said determined condition of the patient.

16. The system of claim 1, wherein the processing unit is included in the control unit of the occlusive system.

17. The system of claim 1, further comprising means for sending an alarm to a user if the detection criterion of atrophy of the natural conduit is fulfilled.

18. The occlusive system of claim 1, consisting of an artificial urinary sphincter.

19. The system of claim 1, said system being an occlusive hydraulic system wherein:
the occlusive element is an inflatable cuff comprising a variable volume of fluid;
the activation device comprises a peristaltic pump configured to transfer fluid between the cuff and a reservoir; and
the displacement parameter is an angular travel described by the pump relative to a reference position to obtain a given compression of the conduit.

20. The occlusive system defined by claim 8 wherein the actuation device comprises an actuator coupled to said mobile wall which operates to move said wall.

21. The occlusive system defined by claim 8 wherein the displacement sensor is a position sensor for determining the position of the mobile wall.

22. The occlusive system defined by claim 20 wherein a displacement applied by said actuator to the movable wall to produce a given pressure of fluid in the reservoir produces a predetermined compression of the natural conduit.

23. The occlusive system defined by claim 20 wherein the actuation device comprises an actuator coupled to said mobile wall which operates to move said wall and movement of the wall provided by said actuator is based on measurement of the pressure in the hydraulic circuit.

24. The occlusive system defined by claim 1 wherein the the pressure sensor is arranged on a wall of the reservoir to provide measurement of the fluid pressure in the reservoir.

25. The occlusive system defined by claim 1 the pressure sensor is arranged on the inflatable cuff to directly measure the pressure on the natural conduit.

26. The occlusive system defined by claim 1 wherein the occlusive element is the band placed around the conduit to be occluded, and a variation in tension of the band varies the compression exerted on the natural conduit to be occluded.

27. The occlusive system defined by claim 26 wherein the band is connected by a mechanical transmission element to an activation device.

28. The occlusive system defined by claim 27 wherein the mechanical transmission element is a cable.

29. The occlusive system defined by claim 27 wherein the activation device varies at least one of the travel and tension of the mechanical transmission element.

* * * * *